United States Patent [19]
Lipp et al.

[11] Patent Number: 5,676,968
[45] Date of Patent: Oct. 14, 1997

[54] TRANSDERMAL THERAPEUTIC SYSTEMS WITH CRYSTALLIZATION INHIBITORS

[75] Inventors: Ralph Lipp; Jutta Riedl; Johannes Tack, all of Berlin, Germany

[73] Assignee: Schering Aktiengesellschaft, Berlin, Germany

[21] Appl. No.: 433,557

[22] Filed: May 3, 1995

Related U.S. Application Data

[63] Continuation of Ser. No. 232,099, Apr. 29, 1994, abandoned.

[30] Foreign Application Priority Data

Oct. 31, 1991 [DE] Germany ............... 41 36 057.5
Mar. 27, 1992 [DE] Germany ............... 42 10 711.3

[51] Int. Cl.$^6$ ........................................ A61F 13/02
[52] U.S. Cl. ............................... 424/448; 424/449
[58] Field of Search ............................ 424/448, 449

[56] References Cited

U.S. PATENT DOCUMENTS

| | | | |
|---|---|---|---|
| 4,637,930 | 1/1987 | Konno | 424/28 |
| 5,122,543 | 6/1992 | Khanna | 514/772.5 |

FOREIGN PATENT DOCUMENTS

| | | |
|---|---|---|
| 0 208 395 | 1/1987 | European Pat. Off. . |
| 0 289 977 | 11/1988 | European Pat. Off. . |
| 0 421 454 | 4/1991 | European Pat. Off. . |
| 0 450 986 | 10/1991 | European Pat. Off. . |
| 089017 | 7/1979 | Japan . |
| 225010 | 12/1983 | Japan . |
| 251534 | 11/1991 | Japan . |
| 91/05529 | 5/1991 | WIPO . |

*Primary Examiner*—D. Gabrielle Phelan
*Attorney, Agent, or Firm*—Millen, White, Zelano & Branigan, P.C.

[57] ABSTRACT

A transdermal therapeutic system is described, which is characterized in that it contains a crystallization inhibitor and optionally penetration enhancer in an active ingredient-containing adhesive matrix.

10 Claims, 1 Drawing Sheet

TRANSDERMAL THERAPEUTIC SYSTEMS WITH CRYSTALLIZATION INHIBITORS

This is a continuation, of application Ser. No. 08/232/09 filed Apr. 29 1994 now abandoned.

The invention relates to transdermal therapeutic systems, which make available active ingredients to the organism through the skin and are characterized in that crystallization inhibitors are contained in the active ingredient-containing matrix.

Transdermal therapeutic systems (TDS) are, as is generally known, plasters made of many layers, which are attached to the skin and which continuously release the active ingredient percutaneously over a prolonged period. Transdermal therapeutic systems essentially consist of a cover film impermeable to water, penetration enhancers and active ingredients, a matrix, which comprises the skin contact adhesive, penetration enhancer and pharmaceutical substance, and a detachable protective film.

High concentrations of dissolved active ingredient in the matrix of transdermal therapeutic systems generally make possible a high flow of active ingredients through the skin. In particular, there have been frequent reports recently of so-called supersaturated systems, which make possible the desired high transdermal flow Of pharmaceutical substances (K. H. Ziller and H. H. Rupprecht, Pharm. Ind. 52, No. 8 (1990), 1017–1022).

A problem of such supersaturated solutions is the insufficient storage stability. Since easily crystallizing compounds are involved in the incorporated active ingredients, crystallization processes must be expected during the storage. This tendency toward crystal formation or toward crystal growth respectively is known, for example, in the case of suspensions and supersaturated solutions of steroid hormones (M. Kuhnert-Brandstätter et al., Sci. Pharm. 35 (1967) 4, 287–297). This phenomenon also applies to supersaturated solutions of poorly soluble substances in acrylate adhesive-enhancer mixtures.

Because of the crystallization process, the portion is shifted from dissolved to crystallized active ingredient. In this connection, optionally even the saturation concentration of the active ingredient in the system can fall short (Jian-wei Yu et al., Drug Development and Industrial Pharmacy 17, 1991, 1883 ff). In addition, crystal growth leads to the reduction of the crystal surface, by which the rate of solution is reduced during the administration.

To prevent crystallization processes in transdermal therapeutic systems and to be able to administer the therapeutically desired dose continuously, crystallization inhibitors are added according to the invention (FIG. 1). By the addition of crystallization inhibitors, a high portion of active ingredient remains dissolved during the storage time. The thus achieved physical stability of the transdermal systems obtained is a basic requirement for the use in practice. Transdermal therapeutic systems, in which crystallization inhibitors are incorporated according to the invention, are distinguished by very good in vitro active ingredient release. Simultaneously, crystallization processes of the active ingredients due to storage are prevented in the TDS according to the invention (Table 1). They are therefore particularly suitable to make the active ingredient continuously bioavailable in humans in therapeutically relevant doses. Thus, for example, a 17β-estradiol-TDS in the presence of a crystallization inhibitor such as silicon dioxide indicated clearly less tendency toward crystal formation than a comparison-TDS without a silicon dioxide additive. While in the system according to the invention no crystal growth was noted over the observation period of 8 months at room temperature storage, large crystals (~730 μm) were formed in the system without crystallization inhibitors (Table 1). As crystallization inhibitors, highly dispersed silicon dioxide or macromolecular substances are suitable. As macromolecular substances, there can be mentioned, for example, polyvinylpyrrolidones with an average molecular weight of about 1,000 to 2,000,000 (for example, Kollidon$^{(R)}$ 12 PF, Kollidon$^{(R)}$ 17 PF, Kollidon$^{(R)}$ 25 PF, Kollidon$^{(R)}$30, Kollidon$^{(R)}$ 90 of the BASF company, vinylpyrrolidone-vinyl acetate copolymers (such as Kollidon$^{(R)}$ VA 64 of the BASF company), crosslinked polyvinylpyrrolidones (such as Kollidon$^{(R)}$ CL of the BASF company), polyvinyl alcohol, hydroxypropyl cellulose, ethyl cellulose, gelatin, starch (derivatives), dextrins and dextrans, such as, for example, α-, β- and γ-cyclodextrin, dimethyl-βcyclodextrin and 2-hydroxypropyl-β-cyclodextrin), sterols (such as cholesterol) or bile acids (such as cholic acid or lithocholic acid).

Here especially the polyyinylpyrrolidones, their copolymers with vinyl acetate and highly dispersed silicon dioxide are distinguished by a high crystallization-inhibitory potency.

Crystallization inhibitors can be used in all known transdermal systems, such as, for example, in polyacrylate systems or in systems based on silicon or synthetic rubber skin contact adhesives, in which the inhibitor is incorporated in concentrations of 0.1 to 40% by weight relative to the total weight of the matrix. In addition to the skin contact adhesive, active ingredient and crystallization inhibitor, the matrix optionally contain penetration enhancers, and all known penetration enhancers and their mixtures are used in the usual concentrations.

Suitable as penetration enhancers, for example, are: monovalent and multivalent alcohols with up to 24 carbon atoms, such as 1,2-propanediol, 1,3-propanediol, 1,2-ethanediol, glycerol or lauryl alcohol; free carboxylic acids with up to 24 carbon atoms, such as lauric acid; fatty acid esters with up to 24 carbon atoms in the fatty acid component and up to 20 carbon atoms in the monovalent or multivalent alcohol component, such as isopropyl myristate, glycerol monopalmitate, dodecanoyl acetate; terpenes, amides, urea and mixtures of these penetration enhancers.

The concentrations of the penetration enhancers or the mixtures of the above-mentioned classes of substances can lie between 0.5 and 40% by weight relative to the total weight of the matrix.

Preferred concentration ranges for 1,2-propanediol are 15–25% by weight, for fatty acid esters, free carboxylic acids and alcohols with 8–24 carbon atoms 0.5–15% by weight, and enhancer mixtures, which are possible in mixing ratios of 1:10 to 10:1, for example, for 1,2-propanediol and lauric acid, 5–40% by weight, preferably 20–30% by weight, relative to the finished matrix.

Active ingredients, which are suitable for the production of transdermal systems according to the invention, are preferably those that are poorly soluble or insoluble in usual adhesive systems and crystallize well, such as, for example, steroid hormones, such as: gestagenically effective steroid hormones, such as, for example, 13-ethyl-17β-hydroxy-18, 19-dinor-17α-pregn-4-en-20yl-one (=levonorgestrel), 13-ethyl-17β-hydroxy-18,19-dinor-17α-pregna-4, 15-dien-20yn-3-one (=gestodene), 13-ethyl-17β-hydroxy-11-methylene-18, 19-dinor-17α-pregn-4-en-20yn (=desorgestrel) or 13-ethyl-11-methylene-17β-hydroxy-18, 19-dinor17αpregn-4-en-3-one (3-keto-desogestrel).

Estrogenically effective steroid hormones, 3-hydroxy-1, 3, 5-(10)-estratrien-17-one (=estrone), 1,3,5(10)-estratriene-3, 17β-diol (=estradiol) or 1,9-nor-17α-pregna-1,3,5(10)-trien-20yn-3, 17β-diol (=ethinylestradiol), 17β-hydroxy-19-nor-17α-pregn-4en-20yn-3-one (=norethisterone acetate), 14α,17α-ethano-1,3,5(10)-estratriene-3, 17β-diol (=cyclodiol) and 14α,17α-ethano-1,3,5(10)-estratriene-3, 16α,17β-triol (=cyclotriol) and combinations of these gestagens and estrogens.

Androgenically effective steroid hormones, such as 17β-hydroxy-4-androsten-3-one (=testosterone) and its esters or 17β-hydroxy-1α-methyl-5α-androsten-3-one (=mesterolone).

Antiandrogenically active steroid hormones, such as 17α-acetoxy-6-chloro-1β, 2β-dihydro-3H-cyclopropa[1,2]-pregna-1,4,6-triene-3,20-dione (=cyproterone acetate).

Corticoids, such as 11β,17α,21-trihydroxy-4-pregnene-3,20-dione (=hydrocortisone), 11β,17α,21-trihydroxy-1,4-pregnadiene-3,20-dione (=prednisolone), 11β,17α,21-trihydroxy-6α-methyl-1, 4-pregnatriene-3,20-dione (=methylprednisolone) and 6α-fluoro-11β, 21-dihydroxy-16α-methyl-1,4-pregnadiene-3,20-dione (=diflucortolone) and their esters.

Suitable active ingredients are further:

Ergoline derivatives, such as lisuride, [=3-(9,10-didehydro-6-methyl-8α-ergolinyl)-1, 1-diethylurea], bromolisuride [=3-(2-bromo-9, 10-dehydro-6-methyl-8α-ergolinyl-1,1-diethylurea], terguride [=3-(6-methyl-8α-ergolinyl-1,1-diethylurea] and proterguride [=3-(6-propyl-8α-ergolinyl)-1,1-diethylurea].

Antihypertensive agents, such as 7α-acetylthio-17α-hydroxy-3-oxo-4-pregnene-21-carboxylic acid-γ-lactone (=spironolactone) and 7α-acetylthio-15β,16β-methylene-3-oxo-17αpregna-1, 4-diene-21, 17-carbolactone (=mespirenone).

Anticoagulants, such as 5-[hexahydro-5-hydroxy-4-(3-hydroxy-4-methyl-1-octen-6-ynyl)-2(1H)-pentalenylidene)]-pentanoic acid (=iloprost) or (Z)-7-[(1R,2R,3R,5R)-5-chloro-3-hydroxy-2-[(E)-(3R)-3-hydroxy-4, 4-dimethyl-1-octenyl]-cyclopentyl]-5-heptenoic acid (=nocloprost).

Psychopharmacological agents, such as 4-(3-cyclopentyloxy-4-methoxy-phenyl-2-pyrrolidone (=rolipram) and 7-chloro-1,3-dihydro-1-methyl-5-phenyl-2H-1, 4-benzodiazepin-2-one (=diazepam).

Organic nitro compounds, such as isosorbide dinitrate [=1,4,3,6-dianhydro-D-glucitol-dinitrate].

Beta blockers, such as propanolol {=1-[(1-methylethyl)-amino]-3-(1-naphthyloxy-2-propanolol}, mepindolol {=1-[(1-methylethyl)-amino]-3-[(2-methyl-1H-inol-4-yl)-oxy]-2-propanol} and carazolol {=2-(9H-carbazol-4-yloxy)-3-[(1-methethyl)-amino]-2-propanol}.

Carotenoids, such as α-carotene and β-carotene.

β-carbolines are another group, such as 5-isopropyl-4-methyl-β-carboline-3-carboxylic acid-ethyl ester and 5-isopropyl-4-methoxymethyl-β-carboline-3-carboxylic acid ethyl ester and other β-carbolines, which are described in European Patent Applications 234,173 and 239,667. Also worth mentioning are highly effective analgesics, such as, for example, 7,8-didehydro-4,5-epoxy-17-methyl-morphinan-3,6-diol (=morphine), 4,5-epoxy-14-hydroxy-3-methoxy-17-methyl-morphinan-6-one (=oxycodone), (−)-(R)-6-(dimethylaminol-4,4-diphenyl-3-heptanone (=levomethadone) or 3,4,5,6-tetrahydro-5-methyl-1-phenyl-1H-2,5-benzoxacin (=nefopam).

Finally, scopolamine can be mentioned as a suitable active ingredient.

It is evident that the transdermal systems according to the invention can also contain mixtures of these active ingredients.

The optimal concentration of active ingredient in the transdermal therapeutic systems according to the invention is dependent, of course, on the type of active ingredient, its effectiveness, the type of penetration enhancers, the adhesive used, etc. and must be determined in the individual case by the preliminary tests well-known to one skilled in galenicals. As a rule, the active ingredient is dosed so that its concentration in the finished matrix is 0.1 to 10% by weight relative to the latter.

The transdermal therapeutic systems according to the invention are preferably constituted so that they consist of a top coating impermeable to the penetration enhancers and optionally also to water, an active ingredient-containing adhesive matrix adhering to the top coating, which contains a crystallization inhibitor and a penetration enhancer, and a removable protective layer.

This simplest form of a transdermal therapeutic system can be produced so that a solution of the adhesive is mixed in a low-boiling solvent with the active ingredient or active ingredient mixture, the penetration enhancer and the crystallization inhibitor, the mixture is applied filmlike on an impermeable removable protective layer, the volatile solvent is removed by heating and the product obtained is covered with a top coating.

Suitable solvents for dissolving the adhesive are, for example, low-boiling alcohols, such as methanol, ethanol or isopropanol, low-boiling ketones, such as acetone, low-boiling hydrocarbons, such as hexane, or low-boiling esters, such as ethyl acetate as well as their mixtures.

This process can be performed so that a solution or suspension of the active ingredient, crystallization inhibitor, penetration enhancers and adhesive in a volatile solvent is applied to a removable protective layer and after the drying at about 60° C. to 90° C. is provided with a plane, impermeable top coating.

As removable protective layers, all films are suitable that are usually used in transdermal therapeutic systems. Such films are, for example, siliconized or fluoropolymer-coated.

As top coating, in this system, for example, 10 to 100 μm thick films of PVC, PVDC or their copolymers EVA, polyethylene or polyester as well as their coextrudates can be used alternatively transparent, pigmented or metallized. The pharmaceutical agent layer applied to this preferably has a thickness of 20 to 500 μm. The release of active ingredients preferably takes place over an area of 5 to 100 $cm^2$.

It is obvious to one skilled in the art that the transdermal therapeutic systems according to the invention can also be configured significantly more complex than the already mentioned simple matrix systems (Yie W. Chien: "Transdermal Controlled Systemic Medications," Marcel Dekker, Inc., New York and Basel, 1987, Dr. Richard Baker: "Analysis of Transdermal Drug Delivery Patents 1934 to 1984" and "Analysis of Recent Transdermal Delivery Patents, 1984–1986 and Enhancers" Membrane Technology & Research 1030 Hamilton Court Menlo Park Calif. 94025 (415) 328–2228). But this generally should provide no significant advantages whatsoever of the systems that justify the increased expense for their production.

EXAMPLES

Figure 1:
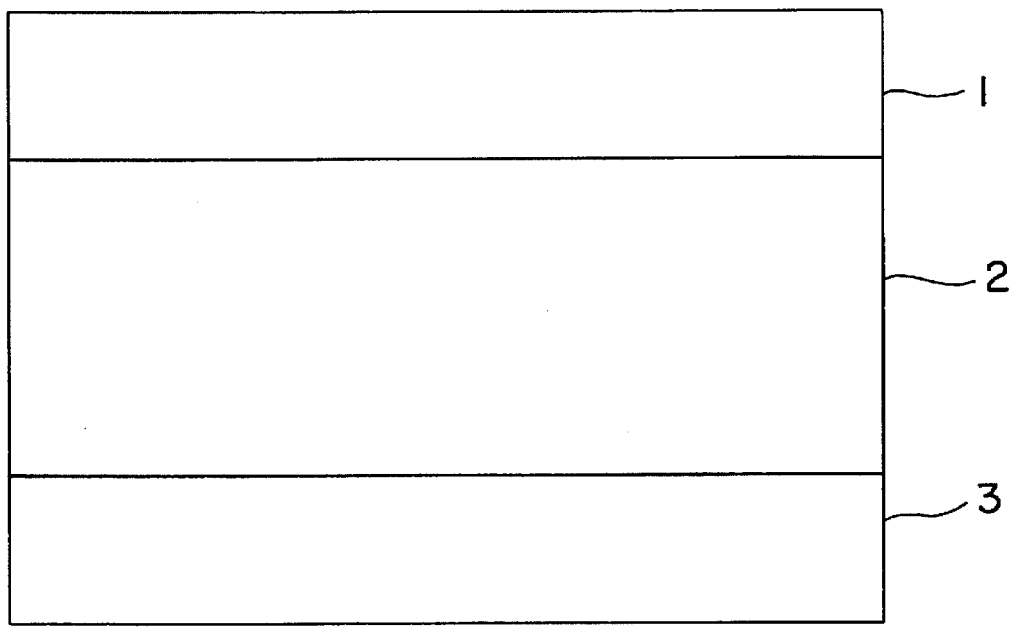
FIG. 1 is a diagrammatic structure of an embodiment of the transdermal therapeutic system having a cover film (1), a matrix (2) containing polyacrylate adhesive, penetration enhancer, a pharmaceutical substance and a crystallization inhibitor and a peeling-off film (3).

The following embodiments are used for a more detailed explanation of the invention:

Example 1

Transdermal therapeutic system with 17β-estradiol (3.3 mg/10 $cm^2$)

3.00 g of 17β-estradiol 35.00 g of 1,2-propanediol and 1.00 g of silicon dioxide, highly dispersed (e.g., Aerosil 200 of the Degussa AG, Frankfurt/M, FRG)

are added in succession to 122 g of a 50% by weight solution of polyacrylate-skin contact adhesive Gelva 2723

(manufacturer: Monsanto Chemical Company, Springfield, Mass.). The forming cloudy mass is then rolled in a high-grade steel vessel to keep the formation of bubbles low during the mixing.

The largely gas bubble-free mass is applied by a knife-over-roll coating device on a siliconized polyester film (peeling-off film: e.g., FDA-PET release liner) so that after the removal of the volatile solvent (ethyl acetate) at 65°–75° C. over 2 to 3 minutes, a uniform film of 100 g/m$^2$ develops. Then, it is laminated with a PVDC cover film (Saran 18L, 30 µm of the Dow Chemical company, Midland, Mich., USA). The thus obtained laminate is divided by a punching device into individual plasters of 2.5 cm$^2$–25 cm$^2$, preferably 10 cm$^2$ of area, and packed in aluminized bags. After removal of the protective film, the plasters adhere to the skin and can be used for hormone substitution.

Example 2

Transdermal therapeutic system with 17β-estradiol (3.3 mg/10 cm$^2$)

3.00 g of 17β-estradiol 35.00 g of 1,2-propanediol and 1.00 g of cholesterol are added in succession to 122 g of a 50% by weight solution of polyacrylate-skin contact adhesive Gelva 2723 (manufacturer: Monsanto Chemical Company, Springfield, Mass. The forming cloudy mass is then rolled in a high-grade steel vessel to keep the formation of bubbles low during the mixing.

The largely gas bubble-free mass is applied by a knife-over-roll coating device on a siliconized polyester film (peeling-off film: e.g., FDA-PET release liner) so that after the removal of the volatile solvent (ethyl acetate) at 65°–75° C. over 2 to 3 minutes, a uniform film of 100 g/m$^2$ develops. Then, it is laminated with a PVDC cover film (Saran 18L, 30 µm of the Dow Chemical company, Midland, Mich., USA). The thus obtained laminate is divided by a punching device into individual plasters of 2.5 cm$^2$–25 cm$^2$, preferably 10 cm$^2$ of area, and packed in aluminized bags. After removal of the protective film, the plasters adhere to the skin and can be used for hormone substitution.

Example 3

Transdermal therapeutic system with 17β-estradiol 2.00 g of 17β-estradiol 5.00 g of isopropyl myristate and 10.00 g of Kollidon$^{(R)}$ VA 64 are dissolved in 20 g of isopropanol and added to 166 g of Gelva$^{(R)}$ 2723 (50% solution in ethyl acetate). The forming cloudy mass is then rolled in a high-grade steel vessel to keep the formation of bubbles low.

The production of the plasters takes place as described in example 1.

Example 4

Transdermal therapeutic system with 17β-estradiol 4.00 g of 17β-estradiol 12.00 g of Kollidon$^{(R)}$ 12 PF and 35.00 g of 1,2-propanediol are dissolved in 20 g of isopropanol and added to 98 g of Gelva$^{(R)}$ 2723 (50% solution in ethyl acetate). The forming cloudy mass is then rolled in a high-grade steel vessel to keep the formation of bubbles low.

The production of the plasters takes place as described in example 1.

Example 5

Transdermal therapeutic system with gestodene 2.00 g of gestodene 5.00 g of isopropyl myristate and 10.00 g of Kollidon$^{(R)}$ VA 64 are dissolved in 20 g of isopropanol and added to 166 g of Gelva$^{(R)}$ 2723 (50% solution in ethyl acetate). The forming cloudy mass is then rolled in a high-grade steel vessel to keep the formation of bubbles low.

The production of the plasters takes place as described in example 1.

Example 6

Transdermal therapeutic system with gestodene 4.00 g of gestodene 12.00 g of Kollidon$^{(R)}$ 12 PF and 35.00 g of 1,2-propanediol are dissolved in 20 g of isopropanol and added to 98 g of Gelva$^{(R)}$ 2723 (50% solution in ethyl acetate). The forming cloudy mass is then rolled in a high-grade steel vessel to keep the formation of bubbles low.

The production of the plasters takes place as described in example 1.

Example 7

Transdermal therapeutic system with levonorgestrel 2.00 g of levonorgestrel 5.00 g of isopropyl myristate and 10.00 g of Kollidon$^{(R)}$ VA 64 are dissolved in 20 g of isopropanol and added to 166 g of Gelva$^{(R)}$ 2723 (50% solution in ethyl acetate). The forming cloudy mass is then rolled in a high-grade steel vessel to keep the formation of bubbles low.

The production of the plasters takes place as described in example 1.

TABLE 1

Presence of active ingredient crystals in 17-β-estradiol-TDS with and without SiO$_2$ as crystallization inhibitor

| Composition of the TDS matrix (per 100 mg) | Maximum crystal size after RT storage over | | |
|---|---|---|---|
| | 1 month | 3 months | 8 months |
| 71.6 mg of acrylate adhesive, 24 mg of 1,2-propanediol, 3.3 mg of E$_2$, 1.1 mg of SiO$_2$, = example 1 | <6 µm | without crystals | without crystals |
| 72.7 mg of acrylate adhesive, 24 mg of 1,2-propanediol, 3.3 mg of E$_2$ | ~450 µm | ~400 µm | ~730 µm |

We claim:

1. A transdermal therapeutic system, comprising:
   a) a top coating which is impermeable to water, penetration enhancer and active ingredient, and
   b) an adhesive matrix, adhered to the top coating comprising
      b1) an active ingredient,
      b2) 0.1 to 40% by weight relative to the total weight of the matrix of a vinylpyrrolidone-vinylacetate copolymer as crystallization inhibitor, and
      b3) a skin contact adhesive.

2. The system according to claim 1, wherein the active ingredient, b1) is asteroid hormone.

3. The system of claims 1, wherein the active ingredient, b1), is a steroid hormone, a corticoid, an ergoline group-containing compound, an antihypertensive compound, an anticoagulant compound, a psychopharmacological agent compound, an organic nitro compound, a beta blocker compound, a carotenoid compound, a β-carboline group-containing compound, scopalamine or a mixture thereof.

4. The system of claim 1, wherein the adhesive matrix, b), further comprises a penetration enhancer.

5. The system of claim 1, further comprising a removable protective layer, c), over the adhesive matrix, b).

6. The system of claim 1, wherein the active ingredient, b1), is incorporated in the adhesive matrix, b), in a concentration of 0.1 to 10% by weight relative to the total weight of the matrix.

7. The system of claim 1, wherein the top coating, a), is a film of polyvinyl chloride, polyvinylidene chloride, ethylene/vinyl acetate copolymer, polyethylene, polyester, copolymers thereof or coextrudates thereof.

8. The system of claim 7, wherein the top coating has a thickness of 10–100μm.

9. The system of claim 1, wherein the adhesive matrix, b), has a thickness of 20 to 500μm and a surface opposite the surface adhered to the top coating with a surface area of 5 to 100 cm$^2$.

10. The system of claim 1, wherein the skin contact adhesive is a polyacrylate.

* * * * *

(12) EX PARTE REEXAMINATION CERTIFICATE (10607th)
United States Patent
Lipp et al.

(10) Number: US 5,676,968 C1
(45) Certificate Issued: May 26, 2015

(54) TRANSDERMAL THERAPEUTIC SYSTEMS WITH CRYSTALLIZATION INHIBITORS

(75) Inventors: Ralph Lipp, Berlin (DE); Jutta Riedl, Berlin (DE); Johannes Tack, Berlin (DE)

(73) Assignee: BAYER SCHERING PHARMA AKTIENGESELLSCHAFT, Berlin (DE)

Reexamination Request:
No. 90/012,693, Sep. 20, 2012

Reexamination Certificate for:
Patent No.: 5,676,968
Issued: Oct. 14, 1997
Appl. No.: 08/433,557
Filed: May 3, 1995

Related U.S. Application Data

(63) Continuation of application No. 08/232,099, filed on Apr. 29, 1994, now abandoned.

(30) Foreign Application Priority Data

Oct. 31, 1991 (DE) .................................... 41 36 057
Mar. 27, 1992 (DE) .................................... 42 10 711

(51) Int. Cl.
 *A61K 9/70* (2006.01)
(52) U.S. Cl.
 CPC ............. *A61K 9/7061* (2013.01); *A61K 9/7053* (2013.01)
(58) Field of Classification Search
 None
 See application file for complete search history.

(56) References Cited

To view the complete listing of prior art documents cited during the proceeding for Reexamination Control Number 90/012,693, please refer to the USPTO's public Patent Application Information Retrieval (PAIR) system under the Display References tab.

*Primary Examiner* — Johnny F Railey

(57) ABSTRACT

A transdermal therapeutic system is described, which is characterized in that it contains a crystallization inhibitor and optionally penetration enhancer in an active ingredient-containing adhesive matrix.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-10 are cancelled.

\* \* \* \* \*